(12) United States Patent
Frith et al.

(10) Patent No.: US 8,635,920 B2
(45) Date of Patent: Jan. 28, 2014

(54) PARTICLE DETECTOR

(75) Inventors: Railton Frith, Buckinghamshire (GB); Dorothy Bray, Buckinghamshire (GB); Kadija Benhlassan-Chahour, Villeparisis (FR); Vadim Strizhov, Moscow (RU); Maxim Karban, Moscow (RU)

(73) Assignee: ImmunoClin Limited, London (GB)

( * ) Notice: Subject to any disclaimer, the term of this patent is extended or adjusted under 35 U.S.C. 154(b) by 1015 days.

(21) Appl. No.: 12/092,623

(22) PCT Filed: Nov. 3, 2006

(86) PCT No.: PCT/GB2006/050369
§ 371 (c)(1),
(2), (4) Date: Nov. 6, 2008

(87) PCT Pub. No.: WO2007/052079
PCT Pub. Date: May 10, 2007

(65) Prior Publication Data
US 2009/0078024 A1    Mar. 26, 2009

(30) Foreign Application Priority Data
Nov. 3, 2005 (GB) .................................. 0522461.3

(51) Int. Cl.
*G01N 15/00* (2006.01)

(52) U.S. Cl.
USPC ......................................................... 73/865.5

(58) Field of Classification Search
None
See application file for complete search history.

(56) References Cited

U.S. PATENT DOCUMENTS

| | | | | |
|---|---|---|---|---|
| 3,307,407 A | * | 3/1967 | Berg et al. | 73/432.1 |
| 4,358,677 A | * | 11/1982 | Ruell et al. | 250/216 |
| 5,861,242 A | | 1/1999 | Chee et al. | |
| 6,164,118 A | * | 12/2000 | Suzuki et al. | 73/1.89 |
| 2003/0148401 A1 | * | 8/2003 | Agrawal et al. | 435/7.9 |
| 2005/0190058 A1 | | 9/2005 | Call | |

FOREIGN PATENT DOCUMENTS

| | | |
|---|---|---|
| DE | 3835339 | 4/1989 |
| DE | 10254158 | 6/2004 |
| GB | 2183344 | 6/1987 |
| WO | 2005071393 | 8/2005 |
| WO | 2005073706 | 8/2005 |

OTHER PUBLICATIONS

Gunther, Zac, and Fromherz, Peter, Noninvasive Neuroelectric Interfacing with Synaptically Connected Nail Neurons Immobilized on a Semiconductor Chip, PNAS, Aug. 28, 2001, pp. 10457-10462, vol. 98, No. 18, Germany.
Poghossian, A., Cherstvy, A., Ingebrandt, S., Offenhauser, A., Schoning, M.J., Possibilities and Limitations of Label-Free Detection of DNA Hybridization with Field-Effect-Based Devices, Science Direct, Apr. 30, 2005, pp. 470-480.

* cited by examiner

*Primary Examiner* — Robert R Raevis
(74) *Attorney, Agent, or Firm* — Nancy J. Flint, Esq.; Nancy J. Flint, Attorney At Law, P.A.

(57) ABSTRACT

A particle detector (10) has a particle sensing surface (12) and a detecting layer (13). Provided on the particle sensing surface (12) is a random arrangement of projecting dactyls (15) which form boundaries to confinement cages (14). Only those particles having a size and shape that permits them to fit into the confinement cages between the dactyls are detected. The particle detector (10) advantageously is adapted to identify a large variety of different particles using the same detector.

8 Claims, 14 Drawing Sheets

PARTICLE DETECTOR

TECHNICAL FIELD

The present invention relates to the field of particle detection and, in particular, to a novel particle detector adapted for use in the detection of particles including, but not limited to, biological compounds, non-biological particles such as dust and fibres and organisms such as bacteria and viruses. The present invention additionally relates to a method of fabricating such a particle detector.

BACKGROUND ART

One of the current methods of detecting organic and inorganic particles relies upon the use of channels in combination with a sensing medium to detect the presence of a particle. Where a particle is trapped in the channel, one or more physical properties of the sensing medium is affected. Thus, in WO 2005/071393 a particle detecting device is described in which a fluid microchannel is provided on a substrate. Multiple particle trapping sites are provided within the microchannel with particle specific, trapping substances provided on the surfaces of the microchannel at each trapping site. Trapped particles are identified using, for example, fluorescent labels which bond to the trapped particles.

Similarly, biological detector chips are known in which an array of oligonucleotide probes, for example, are immobilised on a planar substrate such as that described in U.S. Pat. No. 5,861,242. The surface of the detector chip is then exposed to a sample, which may contain the biological particles of interest, and where the biological particles are present these are trapped by bonding to the oligonucleotide probes. Here too, optically active labels are used to bond with the trapped biological particles, for the purposes of identification.

Also, detectors are known for use in identifying the presence of ions in a bulk sample solution such as the ion sensitive field effect transistor (FET) sensor described in WO 2005/073706.

These known detector arrays have the disadvantage of being inherently designed to be highly sensitive to specific biological particles and insensitive to all others. Frequently, however, detection of many different particles is desired. There is, therefore, a perceived need for a detector capable of identifying the presence of a number of different particles, chemical species or biological organisms in a sample.

DISCLOSURE OF THE INVENTION

It is an object of the present invention to provide a particle detector that is more flexible than those known in the prior art in that it is adapted to be capable of detecting the presence in its immediate environment of more than one type of particle or chemical species. In this respect it is to be understood that the term particle is intended to encompass any molecule, organism or other physical body.

The present invention therefore provides a particle detector comprising a substrate having a particle sensing surface and a plurality of projections extending therefrom, the projections being arranged to define spaces therebetween for receiving particles characterised in that the projections are randomly arranged over the particle sensing surface.

In a preferred embodiment the projections are randomly arranged across the particle sensing surface with a fractal dimensional distribution and the average density of the projections may vary across the particle sensing surface with respect to at least one of the axes of the particle sensing surface.

In one embodiment, the particle sensing surface is provided on a first substrate layer and a second substrate layer is provided for detecting the presence of particles proximate to or in contact with the particle sensing surface. The detecting layer may comprise an array of exposed gate charge sensing field effect transistors and ideally the projections are electrically isolated from the particle sensing surface. Furthermore, means may be provided for applying a voltage potential across the particle sensing surface.

The detector is adapted to discriminate between a range of particles having sizes ranging upwards from 10 nm to 10 μm or more.

In a second aspect the present invention provides a method of fabricating a particle detector comprising the steps of: providing a substrate having a particle sensing surface; providing a plurality of projections extending from the particle sensing surface, the projections being arranged to define spaces therebetween for receiving particles characterised in that the projections are randomly arranged over the particle sensing surface.

Ideally, the substrate is etched to form the plurality of projections and the projections are randomly arranged across the particle sensing surface with a fractal dimensional distribution.

In a preferred embodiment the average density of the projections is varied across the particle sensing surface with respect to at least one of the axes of the particle sensing surface.

In a further aspect the present invention provides a method of designing a particle detector having a plurality of projections arranged on a particle sensing surface, the method of designing the particle detector comprising selecting positions for each of the projections using a quasi- or pseudo-random distribution algorithm.

Thus, with the present invention as a result of the inherent random arrangement of the projections across the surface of the detector, and especially in combination with a variation in their density, the detector is capable of distinguishing particles of many different shapes and sizes. Moreover, the detector is capable of discriminating between particles without the need to bond to or label the particles using dyes or biologically active compounds like antibodies.

BRIEF DESCRIPTION OF THE DRAWINGS

Embodiments of the present invention will now be described, by way of example only, with reference to the accompanying drawings, in which.

BEST MODE FOR CARRYING OUT THE INVENTION

Figure 1:
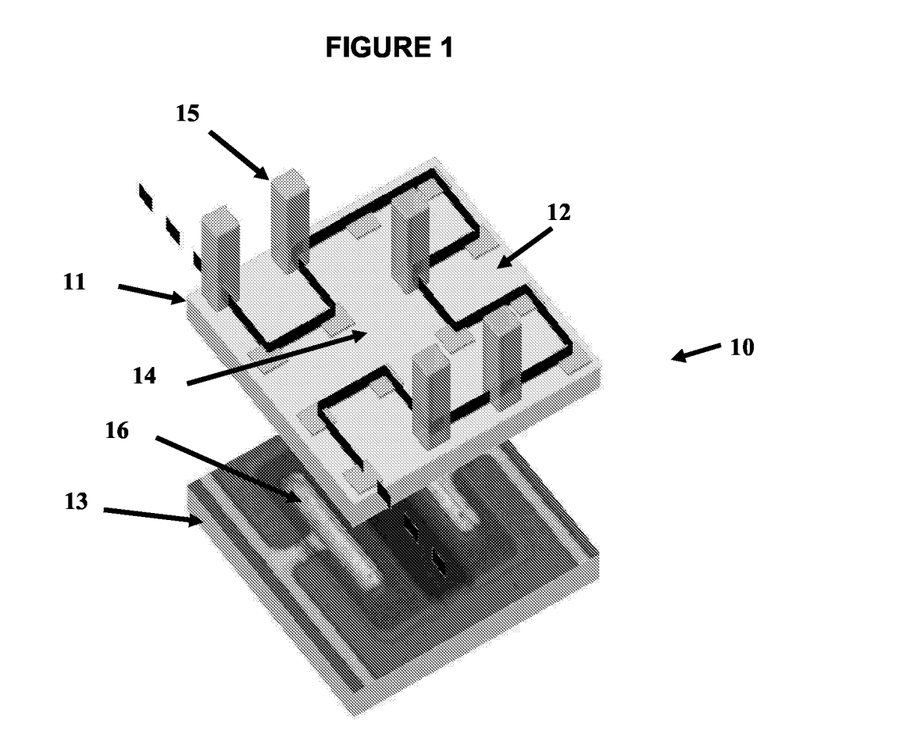
FIG. 1 is a schematic illustration of a small section of a particle detector in accordance with the present invention.

The particle detector 10 illustrated schematically in FIG. 1 generally comprises a trapping layer 11 having a particle sensing surface 12 and a detecting layer 13 which detects the presence of a trapped particle proximate to (i.e. within the sensing range of) or at the particle sensing surface 12. The trapping layer 11 is designed to have the capability to enclose many different particles having differing physical dimensions by means of bounded spaces, referred to herein as confinement cages 14, each of which corresponds generally to the dimensions of one or more particles (and/or their protrusions) to be trapped. Identification of a trapped particle is achieved by identification of a particular confinement cage in which a particle has been trapped.

Each confinement cage 14, one of which is illustrated in FIG. 1, is formed of a region on the particle sensing surface 12 of the trapping layer 11 which may be completely or incompletely bounded by a plurality of projections 15, which are referred to herein as "dactyls". The dactyls 15 are arranged preferably substantially perpendicular to the sensing surface 12. Dactyls arranged at an acute angle to the sensing surface 12 are, though, also envisaged. The dactyls 15 may be of uniform height or may vary in height and although illustrated with a square cross-section, for ease of reference, the dactyls may have any cross-section. Thus, the dactyls 15 restrict the approach of particles to the particle sensing surface 12 to those particles having shapes and/or protrusions which are smaller than the shapes of the confinement cages 14.

The layout of the dactyls 15 across the trapping layer 11 is random, quasi- or pseudo-random. Accordingly, the confinement cages 14, defined between the dactyls, can differ widely both in terms of their dimensions and their shapes which may be regular or irregular. This variation in the shapes and dimensions for the confinement cages across the surface of the particle detector 10 means that a single particle detector is capable of detecting a broad range of different biological and non-biological particles. The design of the arrangement of the dactyls across the particle detector 10 is described in greater detail below.

The trapping layer 11 may be produced from a range of materials, depending on the required application. One example is a semiconductor wafer from/on which the individual dactyls are formed for example by ablation, ion deposition, deep UV etching etc. With the embodiment of FIG. 1, the dactyls 15 are formed so as to be substantially electrically isolated from the particle sensing surface 12 and the underlying detecting layer 13.

Figure 2:
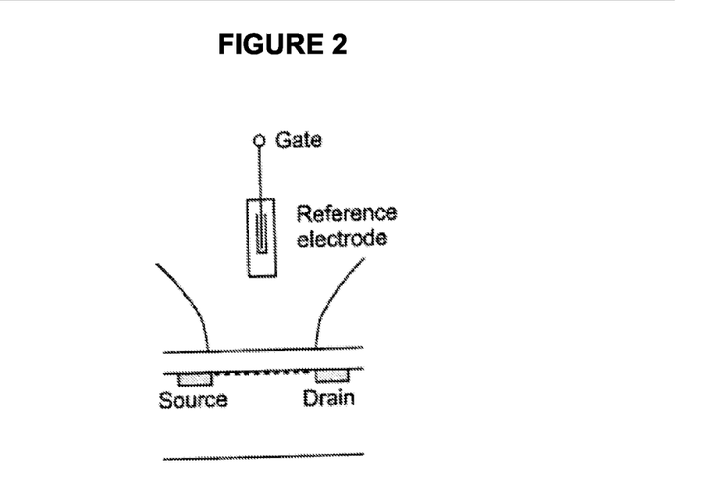
FIG. 2 shows schematically an FET for use with the particle detector of FIG. 1.

In the embodiment illustrated in FIG. 1, the detecting layer 13 comprises an array of individually addressable exposed gate charge sensing field effect transistors (FETs) 16 located beneath the particle sensing surface 12. The FETs 16 enable the spatial location of a confined particle proximate to or on the particle sensing surface 12 to be identified with respect to the particle's confinement cage. An example of a suitable FET is illustrated in FIG. 2. Whilst conventional ion sensing FETs (ISFETs) may be 20 $\mu m^2$ in size, the principle of their function remains substantially the same even at the smaller scale required for the particle detector 10, as the bulk sensing associated with conventional uses of FETs does not apply. Optionally a reference electrode may be provided to enable the charge to be expressed.

It will, of course, be understood that alternative means may be employed for detecting the proximity of particle to the particle sensing surface. For example, an alternative detecting layer may comprise a metalized checkerboard grid provided beneath the particle sensing surface 12 with each square of the grid operated as a nanoscale capacitor in an oscillating electronic circuit.

The metalized checkerboard grid may be substituted by a single metalized path which describes a fractal curve or a spiral in the detecting layer 13. With this embodiment, the time taken for a voltage pulse to travel the metalized path may be used to identify the position of the particle in the confinement cage and multiple reflections allow multiple different particles to be detected as the path difference enables discrimination between the different particles.

In a further alternative, the detecting layer may comprise an array of light emitting diodes (LEDs) embedded in the particle sensing surface 12. Where particles are located in the confinement cages, they will act to at least partially block light emitted by underlying LEDs. Thus, by monitoring the light intensity distribution across the particle detector the trapping of particles in the confinement cages may be detected.

The presence of particles in the confinement cages 14 may alternatively be detected remotely in which case the detecting layer 13 may be omitted. For example, particles may be trapped in the confinement cages by means of an electrical or magnetic field which attracts the particles to the particles sensing surface. After particles positioned outside of the confinement cages have been removed, e.g. by cleaning, the presence of particles in the confinement cages may be detected by means of a scanning probe microscope for example. Alternatively, a high powered laser may be used to scan the surface of the particle detector causing ionisation of the trapped particle or luminescence: the spatial source of the ionisation or luminescence may be detected to enable identification of the particle.

In a further alternative, an alternating voltage may be applied to the surface of the particle detector. This is of use in association with a reference electrode, where the detecting layer comprises an array of FETs. Also, the use of an alternating voltage in association with the natural polarity of the particles to be detected, enhances the detector's ability to discriminate such particles.

For determining the positions of the dactyls on a particle detector, a random number generator using any conventional quasi- or pseudo-random number algorithms may be used or other random number generation technique. For each spatial position on the particle detector, the random number generator is used to determine whether or not a dactyl is to be placed at that position.

Additionally, in order to ensure that the average size of the individual confinement cages varies over the surface of the particle detector and thereby increasing the variety of particles the detector is capable of trapping, the density of the dactyls may also be varied. To change the dactyl density, the decision to place a dactyl at each position is combined with a modulation function that varies the frequency that dactyls are chosen from the random number generator. Modulation functions may include straight line and/or polynomial functions.

When using the modulation function the method of determining the spatial layout of the dactyls over the detector (the placement method) is important. For example, where a random number generator is used to identify random x, y co-ordinates, as well as whether or not a dactyl is to be placed at those co-ordinates, the modulation function will have little impact on dactyl density.

Alternatively, where dactyl placement is determined in 1 dimension by a simple scanned path that spirals/zigzags over the surface of the detector, the combination of a modulation function will provide a random dactyl layout in which the average size of the confinement cages in one dimension will vary. In a similar manner, the dactyls may be arranged over the surface of the detector in 2D paths such as concentric rings or boxes.

Figure 3:
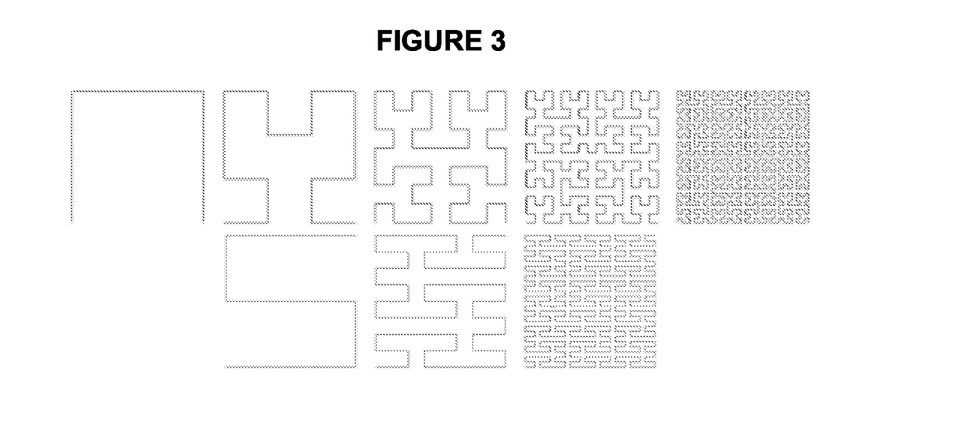
FIG. 3 shows example of square grid Hilbert and Hilbert II curves (of order 1 to 4 and order 1 to 3 respectively)

In a preferred embodiment random dactyl placement is determined in fractal dimension (1<dimension<2) along a fractal path. Some of these dimensions are called curves (e.g. the Hilbert, Peano or Sierpinski curves), that wander around the surface of the detector. When combined with a modulation function, this provides a random dactyl layout in which the average length and width of the confinement cages varies across the surface of the particle detector. Examples of square grid Hilbert and Hilbert II curves are illustrated in FIG. 3. As the average size of the confinement cages in fractal space is a convoluted line, the spatial distribution of the cages is less sensitive to minor defects which may arise during fabrication.

The placement methods described above can be scaled to any suitable construction size. In the case of fractal curves, each line in a fractal curve can be replaced by the same fractal curve so that the path taken is recursive. This means that finer detail can be achieved by increasing the number of recursions or order of the fractal curve. The confinement cages are arranged over the surface of the particle detector so that there is no regular pattern of dactyls at this level. However, repeating patterns of dactyls at 2 or 3 or more orders of magnitude in scale may arise which is of benefit as it enables 'step-and-repeat' fabrication techniques to be employed.

A particle detector in accordance with the present invention that has been modelled using randomly placed, perpendicular dactyls of equal height is described below. Each dactyl has a 5×5 nm cross-section and the detector surface was fixed at 512×512 dactyls (6.55 µm$^2$). It will, of course, be understood that the present invention is not restricted to particle detectors of these dimensions and that any area of detector is envisaged. For example the nanoscale surface of 512×512 dactyls of the modelled particle detector may be scaled to a physical size were there are $10^{12}$ or more dactyl positions. Also, the square grid pitch of 5 nm was chosen purely for ease of modelling. In practice, the placement of the dactyls is not restricted to lie upon a grid and the dactyl dimensions may vary from those employed in this example.

The pseudo-random distribution function for the dactyls of the modelled particle detector is $x=a+b\ \xi^{1/2}$, where a and b are the spatial co-ordinates and $\xi$ is a uniformly distributed random variable. The parameters of the distribution were aligned so that the initial minimal average distance between two dactyls is 35 nm, when $\xi$ tends to zero and the initial minimal average area of the smallest confinement cage formed by the dactyls is 530 nm when $\xi$ tends to 1.

Figure 4:
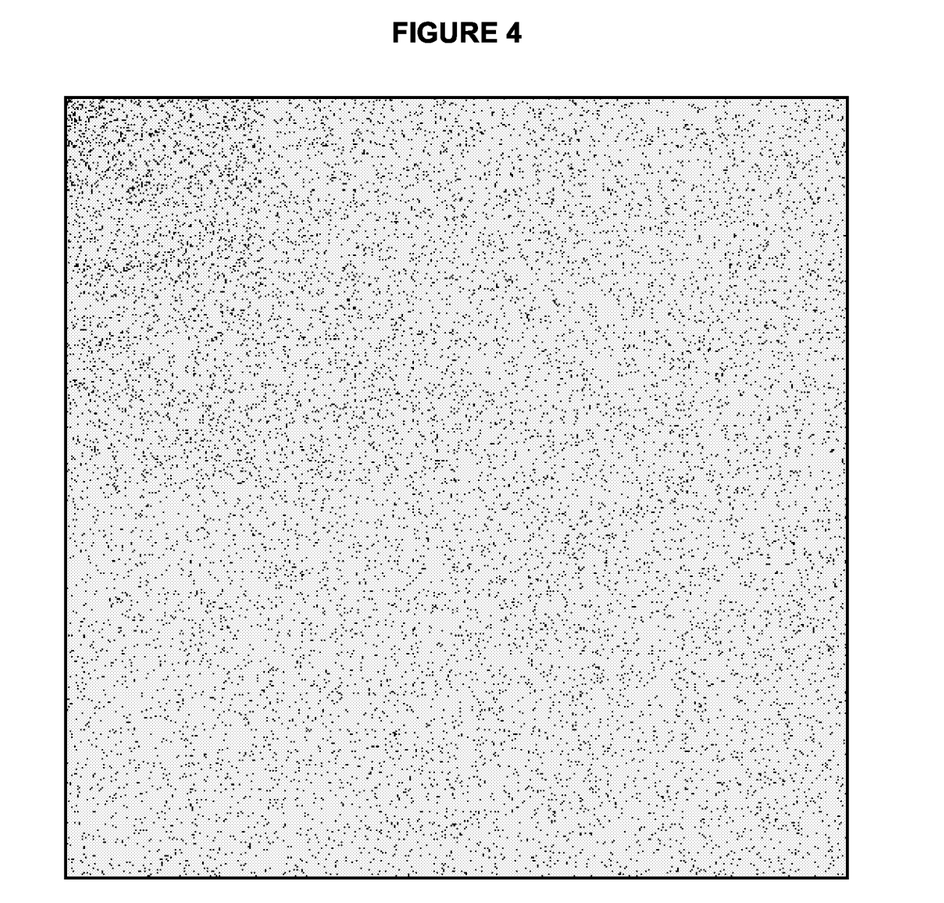
FIG. 4 illustrates the positions of dactyls across the surface of a specimen particle detector in accordance with the present invention.

FIG. 4 illustrates the distribution of dactyls across the surface of the modelled particle detector. A Hilbert curve order 9 was chosen for the disposition of the dactyls across the surface of the particle detector with the path starting at the top left of FIG. 4. The density distribution of the dactyls was reduced with respect to path length (L) from the top left hand corner of the detector. The density reduction was chosen to be proportional to the fourth root of the path length.

Figure 5:
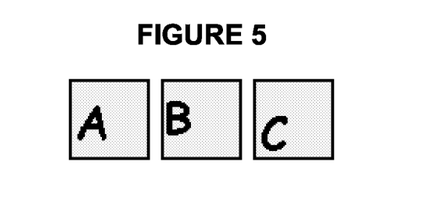
FIG. 5 illustrates three exemplary artificial 2D particles for use in analysing the performance of the particle detector of FIG. 4.

To illustrate the function of the confinement cages defined by the dactyls of the modelled particle detector, three arbitrary and artificial exemplary 2D particles (particle 'A', particle 'B' and particle 'C') are shown in FIG. 5. Each exemplary particle is defined by a plurality of contact points on its perimeter and each exemplary particle has an approximate area bounded by the contact points of 20×20 dactyls (0.01 µm$^2$).

As described earlier, the projecting dactyls prevent particles approaching the particle sensing surface of the particle detector except where a particle or its protrusions has dimensions that are less than the dimensions of a confinement cage which it is close to. The contact points of the exemplary particles are used to determine whether the exemplary particle would fit within the confinement cages defined by the distribution of dactyls across the surface of the detector. Thus, in analysing the modelled particle detector, only where all contact points of an exemplary particle are in contact with the particle sensing surface, and not with one or other of the dactyls, is the confinement cage for that region of the particle sensing surface deemed to be capable of trapping and hence identifying the exemplary particle.

Figure 6:
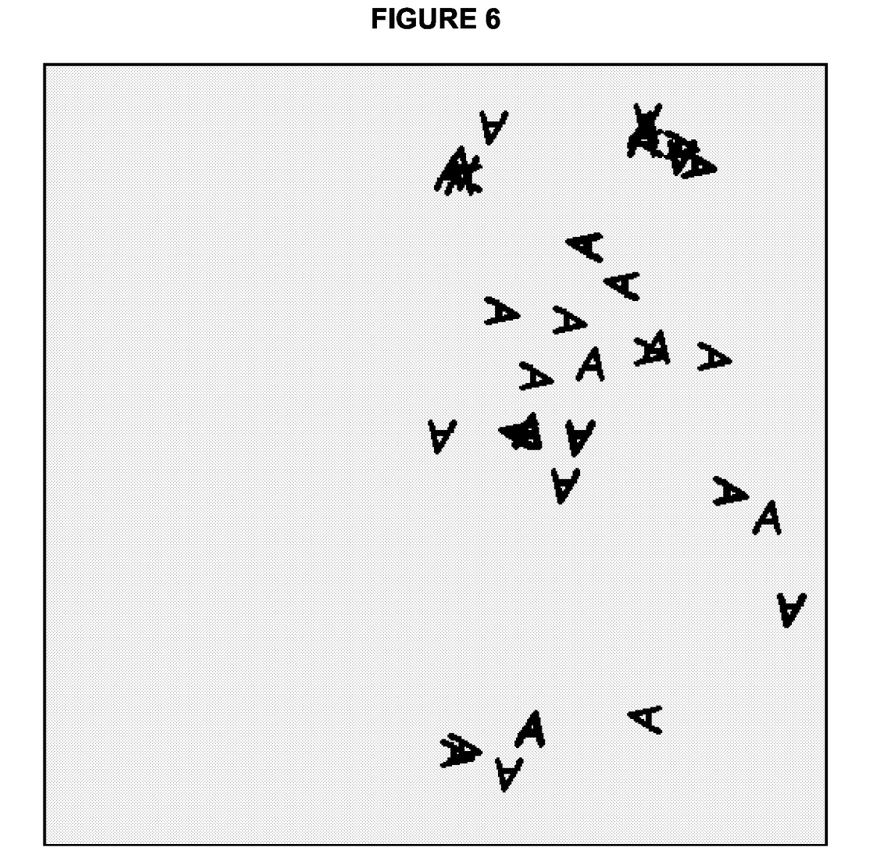
FIG. 6 illustrates locations where the 'A' particle is capable of being trapped between dactyls on the surface of the detector of FIG. 4.
Figure 7:
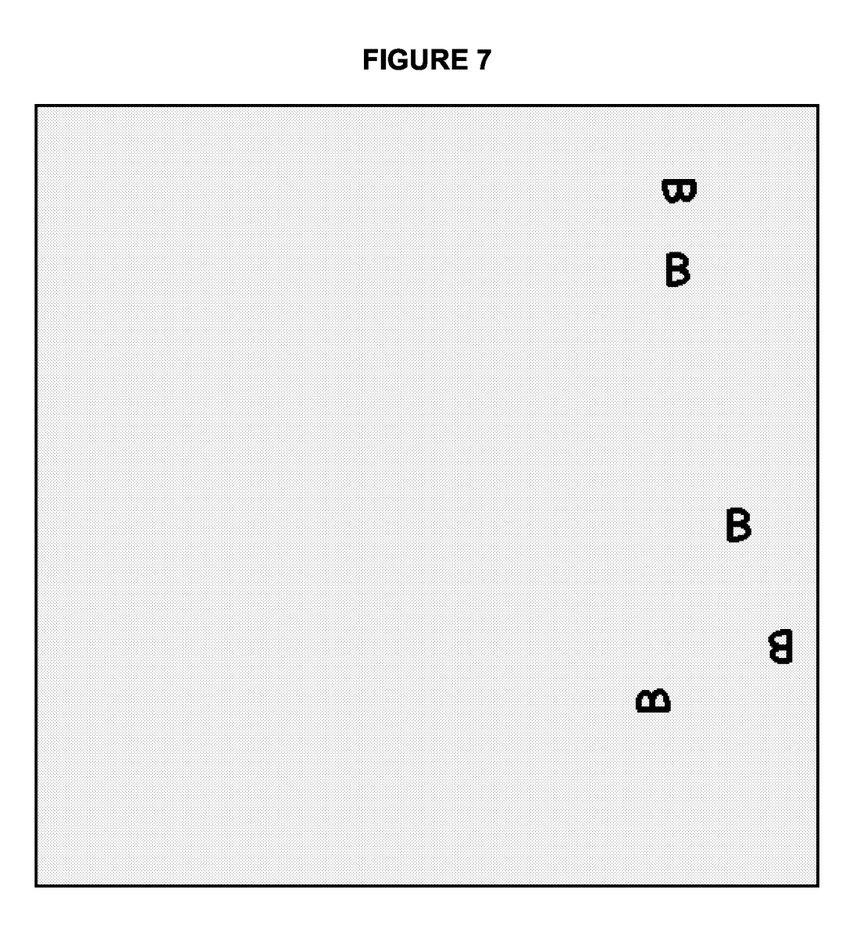
FIG. 7 illustrates locations where the 'B' particle is capable of being trapped between dactyls on the surface of the detector of FIG. 4.

FIG. 6 illustrates positions on the detector surface where the first exemplary particle (particle 'A') was deemed to have been trapped in confinement cages. Similarly, FIG. 7 illustrates those positions on the detector surface where the second exemplary particle (particle 'B') was deemed to have been trapped and FIG. 8 illustrates positions where any or all of the exemplary particles were deemed to be confined.

Figure 8:
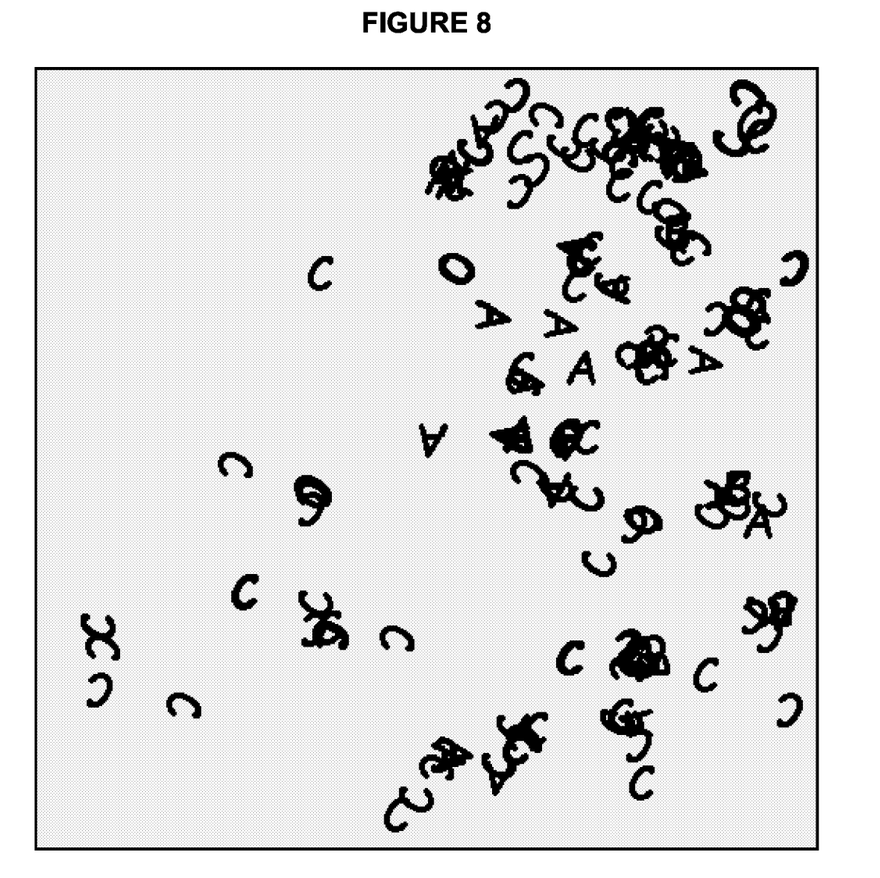
FIG. 8 illustrates locations where any one or more of the three artificial 2D particles is capable of being trapped between dactyls on the surface of the detector of FIG. 4.

As can be seen from FIG. 8, a confinement cage may be of a size which makes it capable of trapping many different particles. In these circumstances the confinement cage may not contribute to particle discrimination in which case it may be rejected (i.e. detection of a particle in that confinement cage is ignored).

Figure 9:
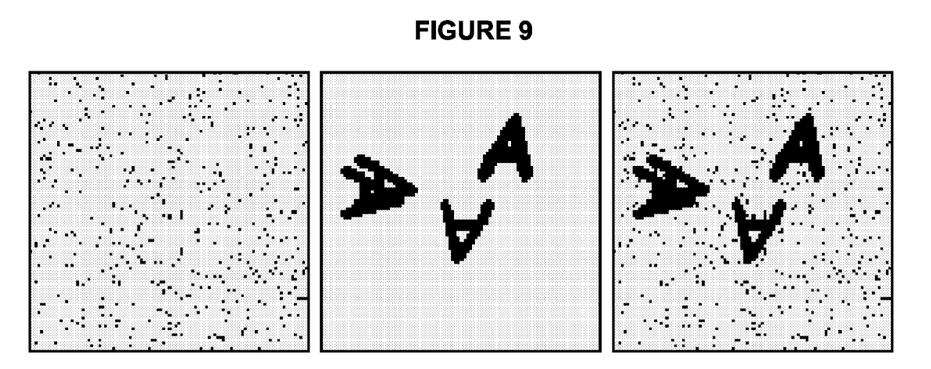
FIG. 9 is an exploded view of a region of the particle detector of FIG. 4 showing dactyls alone, the confinement of 'A' particles alone and dactyls and the confinement of 'A' particles together.
Figure 10:
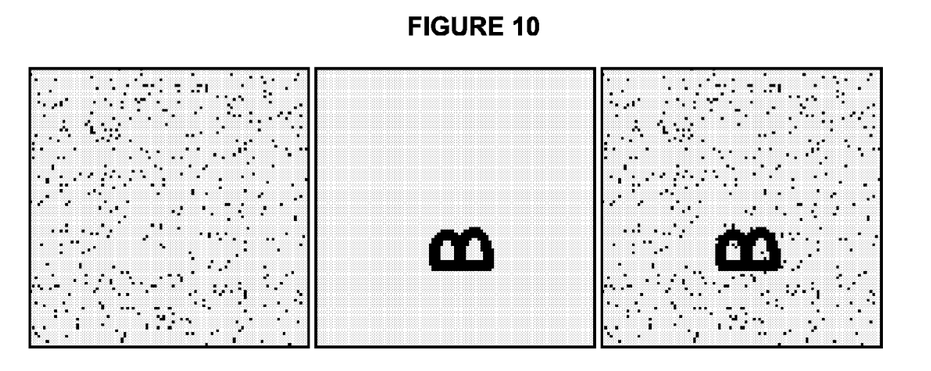
FIG. 10 is an exploded view of a region of the particle detector of FIG. 4 showing dactyls alone, the confinement of 'B' particles alone and dactyls and the confinement of 'B' particles together.
Figure 11:
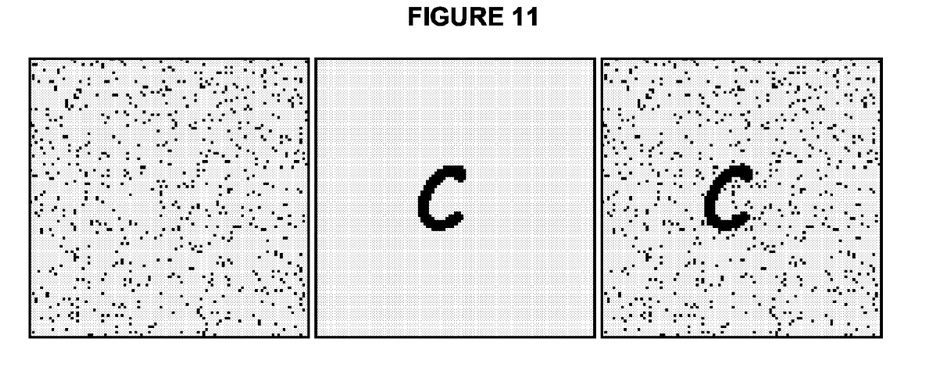
FIG. 11 is an exploded view of a region of the particle detector of FIG. 4 showing dactyls alone, the confinement of 'C' particles alone and dactyls and the confinement of 'C' particles together.
Figure 12:
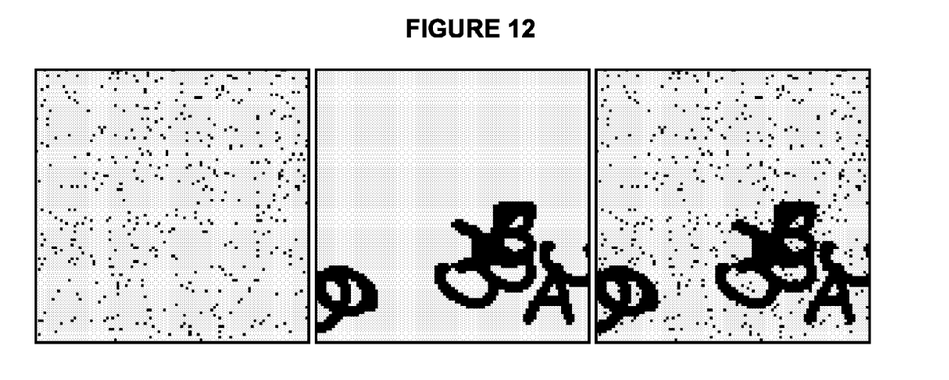
FIG. 12 is an exploded view of a region of the particle detector of FIG. 4 showing dactyls alone, the confinement of all three particles alone and dactyls and the confinement of the particles together.

In FIGS. 9, 10, 11 and 12 exploded (0.25 $\mu m^2$) views of the same area of the surface of the particle detector are shown. In FIG. 9 a series of three images of the area are shown: the first illustrating the positions of dactyls in that area; the second showing the positions of functioning confinement cages i.e. confinement cages in which particle 'A' would fit; and the third showing the positions of the dactyls and 'A' particles in the functioning confinement cages. FIGS. 10 and 11 provide similar illustrations in respect of 'B' particles and 'C' particles and FIG. 12 illustrates all three types of particle.

Figure 13:
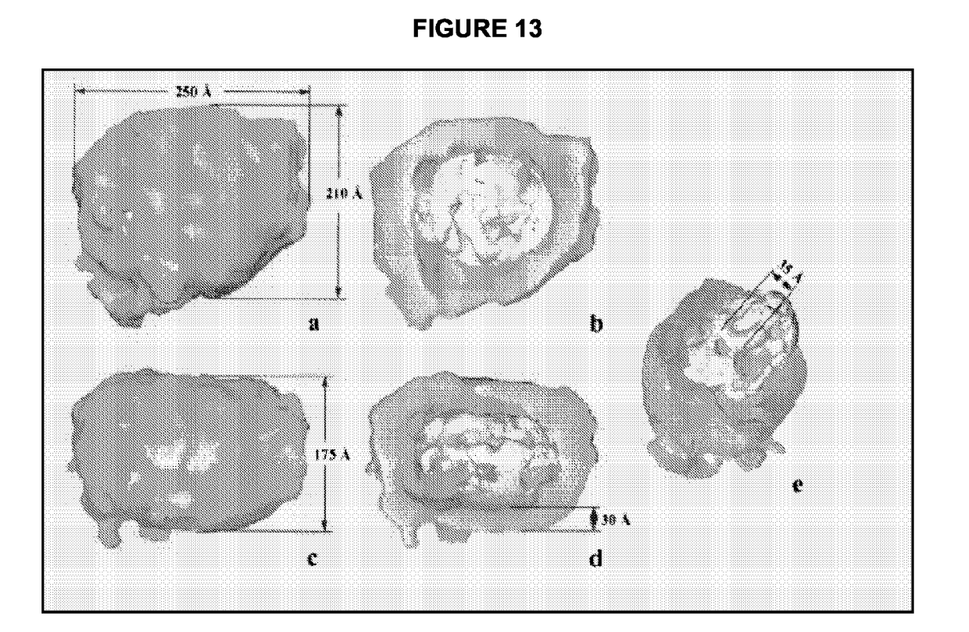
FIG. 13 shows different views of a LDL cholesterol particle.
Figure 14A:
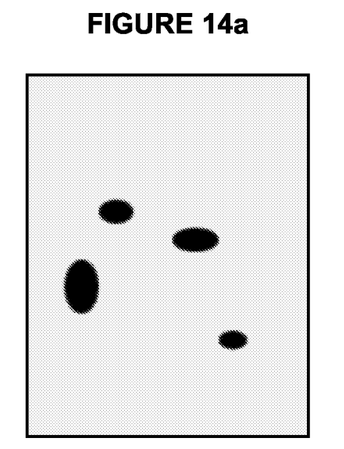
FIG. 14a illustrates a series of different contact surfaces of the LDL cholesterol particle and FIG. 14b shows the same contact surfaces simplistically.
Figure 14B:
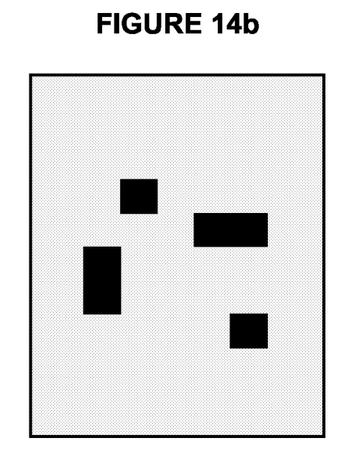

In the following description the use of a particle detector in accordance with the present invention to detect a real particle, the LDL cholesterol particle, is described. In FIG. 13 a particle of LDL cholesterol is illustrated in 3D with the sizes of different dimensions of the particle identified. With these known dimensions of the particle, contact points for the LDL cholesterol particle can be identified and are illustrated in FIGS. 14a and 14b. As the LDL cholesterol particle is capable of rotating in all three dimensions, in FIG. 14a perimeters of different contact surfaces of the 3D LDL cholesterol particle are shown and in FIG. 14b these are presented in the simplified version employed in the following analysis.

Figure 15:
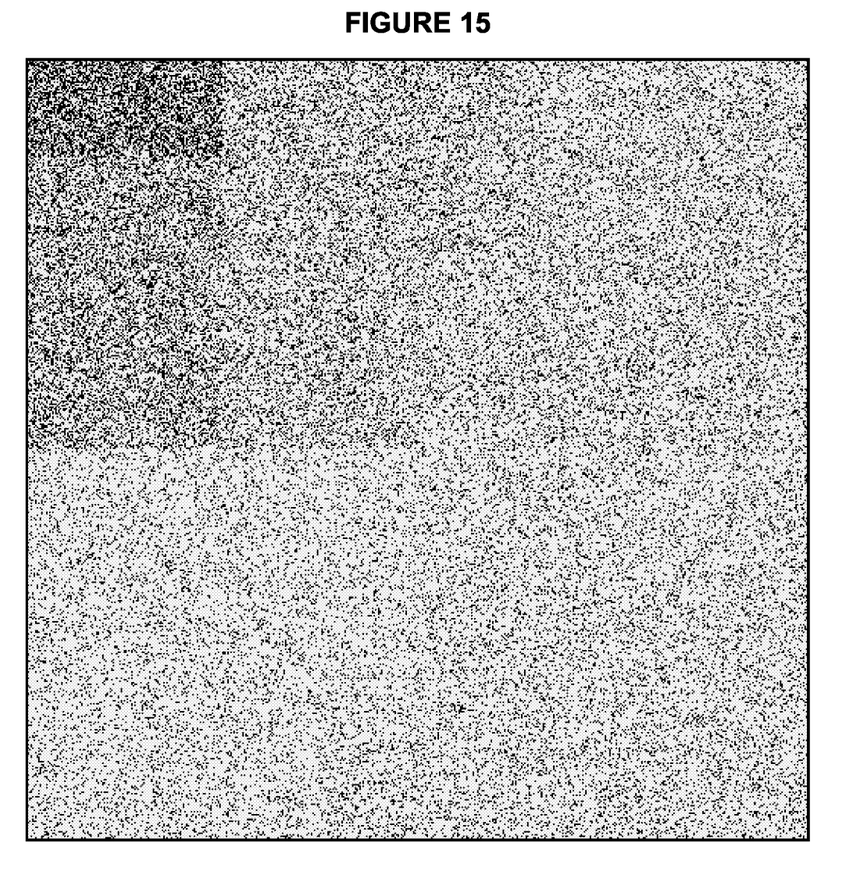
FIG. 15 illustrates the surface of an alternative particle detector having a high but variable density of dactyls, in accordance with the present invention.
Figure 16:
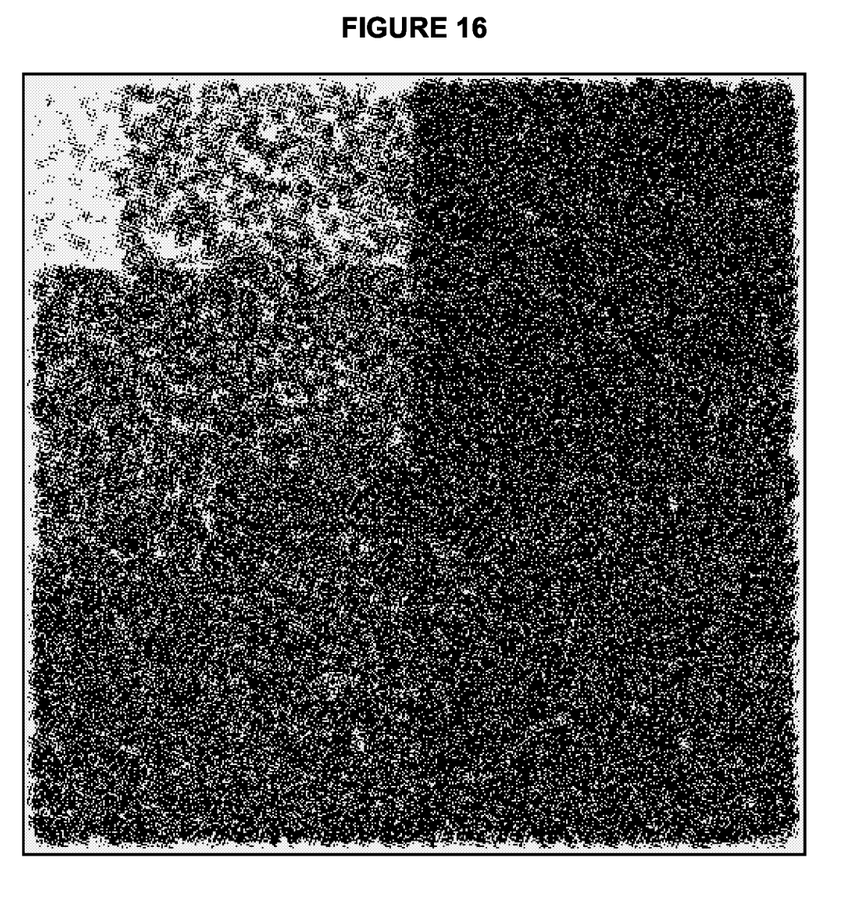
FIG. 16 illustrates where LDL cholesterol particles could be trapped in confinement cages on the surface of the detector of FIG. 15.

A variable high density dactyl detector surface is illustrated in FIG. 15 and in FIG. 16 regions of that surface where the LDL cholesterol particle would be able to contact the sensing surface of the detector are illustrated. Thus, it can be seen that where the density of dactyls is lower, i.e. to the bottom right-hand quadrant of the detector, the opportunities for the cholesterol particle to contact the surface of the detector are high. However, where the density of dactyls is higher, i.e. towards the top left-hand quadrant of the detector, there are less trapping events. Thus for discrimination purposes, the containment cages to the top left quadrant would be most effective.

Figure 17:
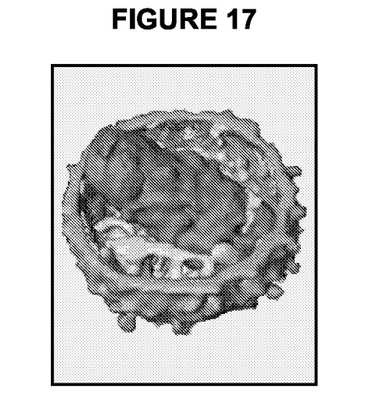
FIG. 17 illustrates an HIV particle.
Figure 18A:
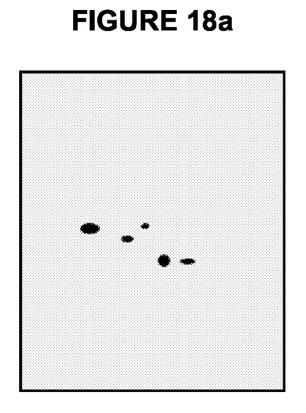
FIG. 18a illustrates a series of different contact surfaces of the HIV particle and FIG. 18b shows the same contact surfaces simplistically.
Figure 18B:
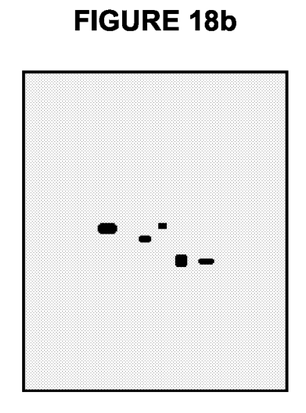
Figure 19:
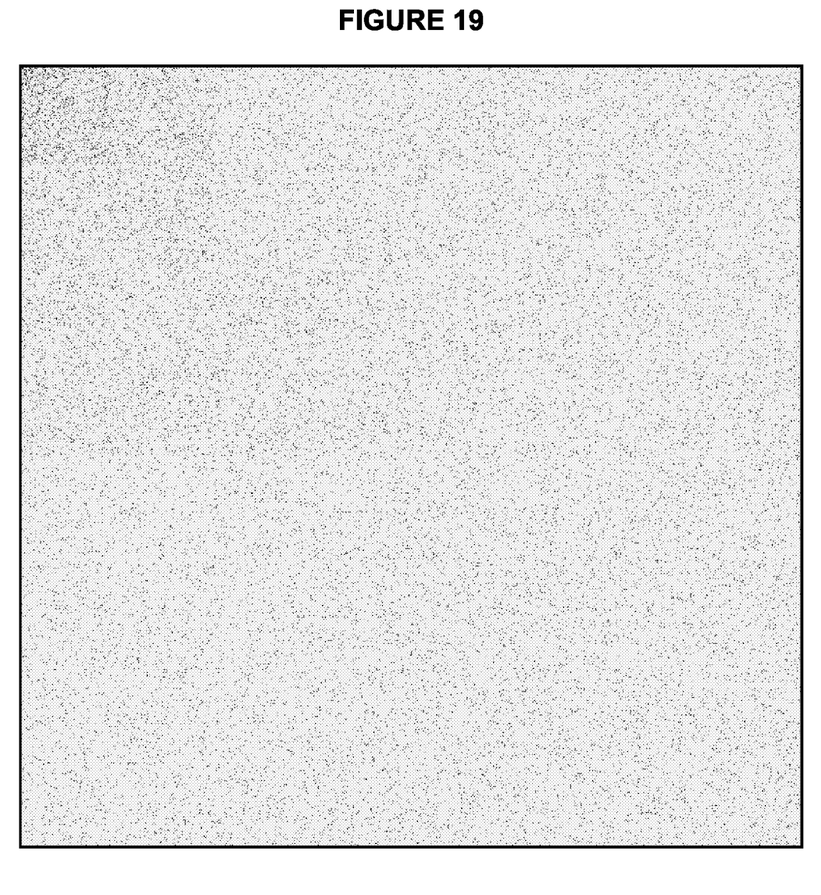
FIG. 19 illustrates the surface of further alternative particle detector in accordance with the present invention.

FIGS. 17 and 18a and 18b illustrate the HIV molecule in the same manner as FIGS. 13 and 14 illustrated the LDL cholesterol molecule. FIG. 19 illustrates a different fractal dactyl detector surface using a Hilbert curve order 10 with 1024×1024 dactyl locations (26.2 $\mu m^2$) and FIG. 20 shows where the HIV molecule could be trapped by confinement cages on the detector.

Figure 20:
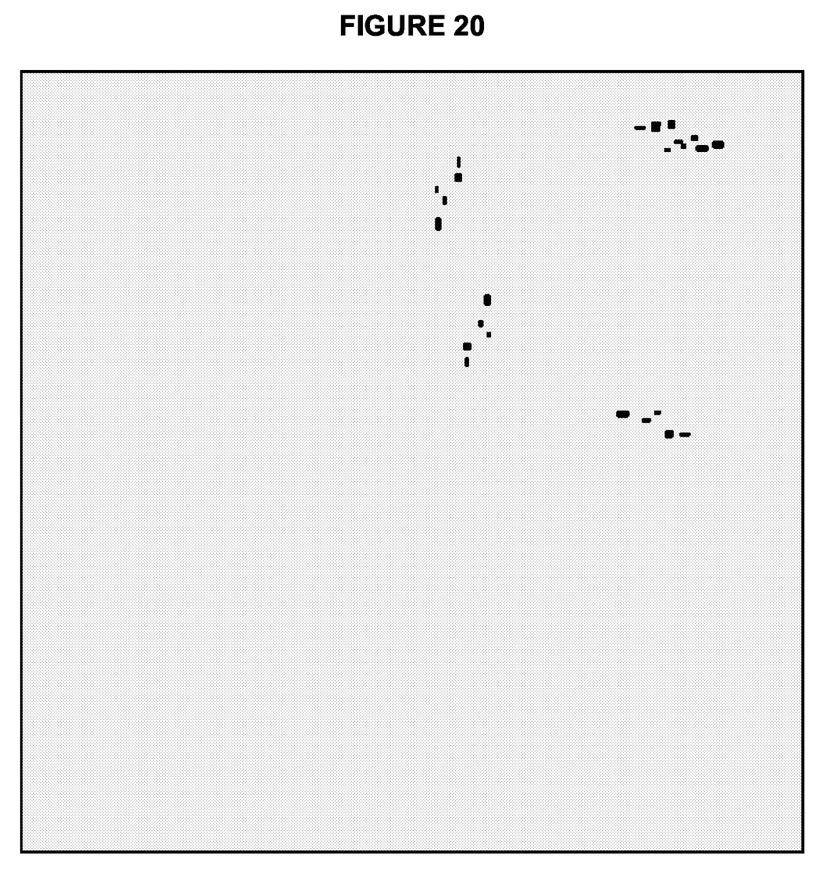
FIG. 20 illustrates where HIV particles could be trapped in confinement cages on the surface of the detector of FIG. 19.
Figure 21:
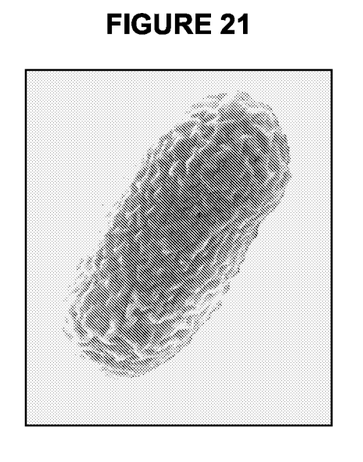
FIG. 21 illustrates an *E coli* bacteria.
Figure 22A:
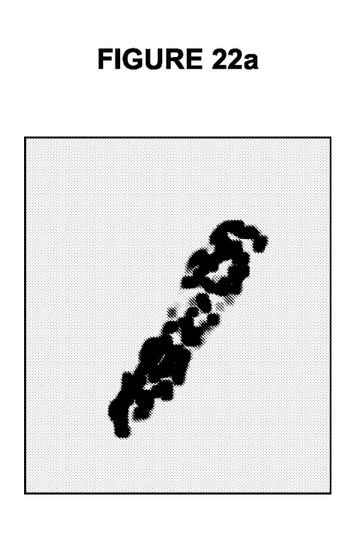
FIG. 22a illustrates a series of different contact surfaces of the *E coli* bacteria and FIG. 22b shows the same contact surfaces simplistically.
Figure 22B:
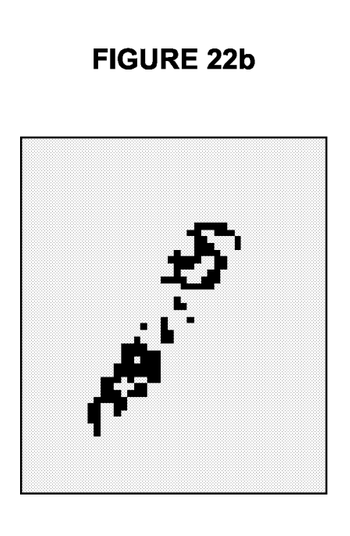
Figure 23:
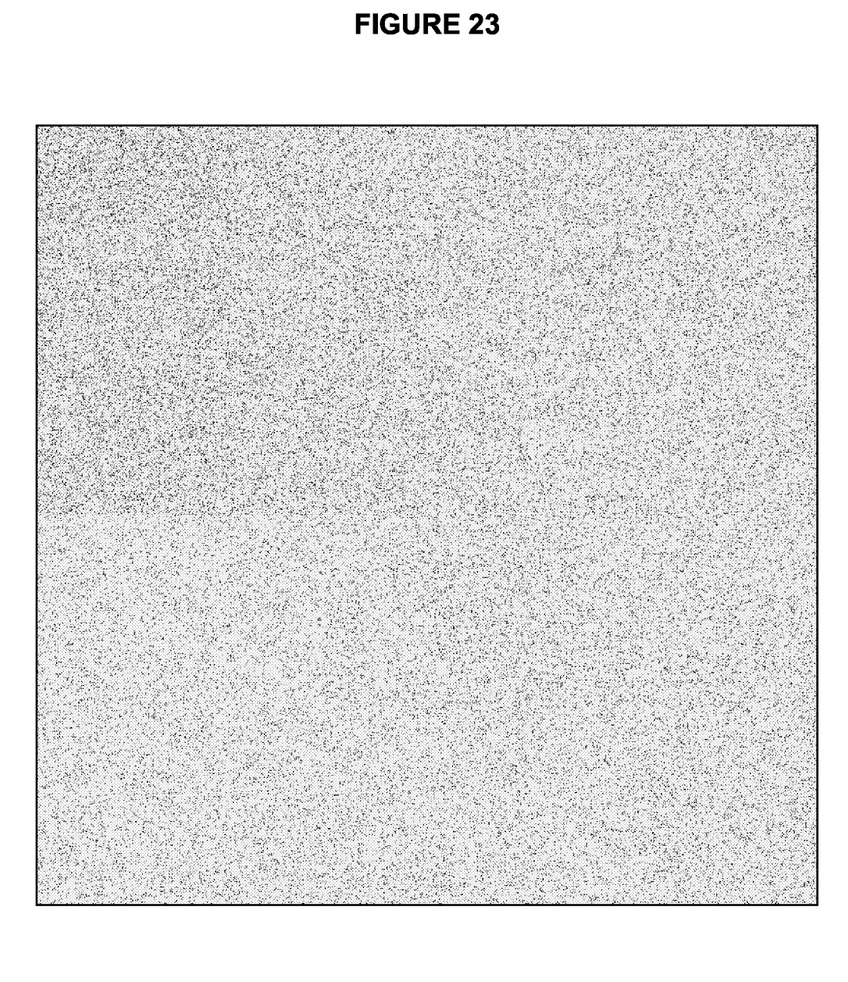
FIG. 23 illustrates the surface of further alternative particle detector in accordance with the present invention.
Figure 24:
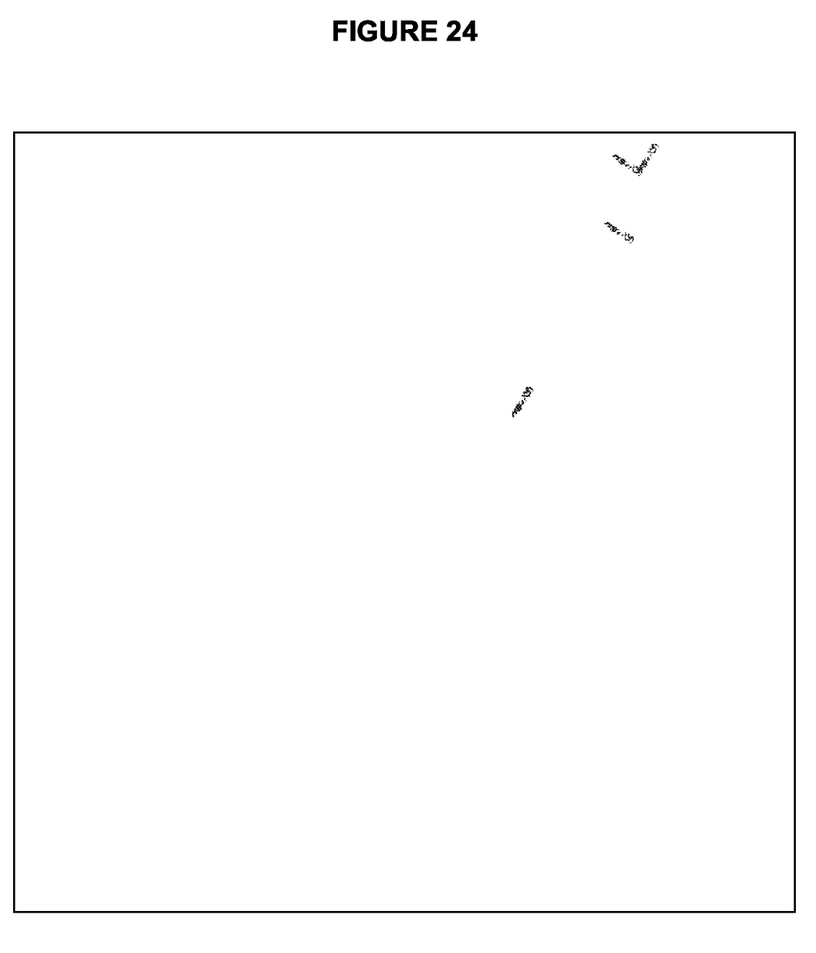
FIG. 24 illustrates where *E coli* bacteria could be trapped in confinement cages on the surface of the detector of FIG. 23.

FIGS. 20 and 21a and 21b illustrate an *E coli* bacteria in the same manner as FIGS. 13 and 14 illustrated the LDL cholesterol molecule. FIG. 22 illustrates a further different fractal dactyl detector surface and FIG. 23 shows where the *E coli* organism could be trapped by confinement cages on the detector.

The detectors described above for LDL cholesterol, the HIV virus and the *E coli* bacteria illustrate the dynamic range of the present invention. The dactyls in FIG. 22 are on a 25 nm grid but this is the same as moving further away from the high density area of the surface when there is one million dactyl locations on a 5 mm square chip.

As has been shown the particle detector described herein, with suitable chosen design parameters, is capable of detecting many different particles both biological compounds, non-biological particles such as dust and fibres and biological organisms such as bacteria and viruses. At its simplest, the particle detector may be analysed to identify those confinement cages which will trap specific particles. This can be based on the known dimensions of particles and/or by sampling with known particles. Additionally, it is not always necessary for the confinement cages to be exclusive to an individual particle. A computer may be programmed to extract information as to which sensors and associated cage(s) have been activated with this data being compared with the reference datum. Identification of a specific particle or combination of particles can be achieved by digital processing techniques (such as pattern matching, neural networks, Fourier analysis or other statistical methods), to enhance detection of specific particles.

Although reference is made herein to a trapping layer and confinement cages, it will be apparent from the foregoing that particles may not be held or restrained within the confinement cages. Instead, reference to confinement and trapping is intended to encompass particles and/or their protrusions having a size which enables them to fit within the boundary of a confinement cage. Furthermore, the confinement cage is not necessarily required to be free of dactyls within the boundary of the confinement cage. For more particles having more complex structures, like the artificial particles illustrated earlier, the contact points of the particle may be discontinuous and arch around dactyls within the confinement cage.

The particle detector of the present invention is to be contrasted with known detectors in the prior art which are restricted in their ability to detect widely varying particles. The inherent random arrangement of the dactyls especially in combination with a variation in their density, results in a detector capable of distinguishing particles of many different shapes and sizes.

The present invention is not intended to be restricted to the details of the specific examples described herein and instead is limited only by the scope of the accompanying claims.

The invention claimed is:

1. A particle detector comprising a first substrate having a particle sensing surface and a plurality of projections extending therefrom formed by etching the first substrate, the projections being arranged to define spaces therebetween for receiving particles where the projections are randomly, quasi-randomly or pseudo-randomly arranged over, in proximity to or in contact with the particle sensing surface.

2. A particle detector as claimed in claim 1, wherein the average density of the projections varies across the particle sensing surface with respect to at least one of the axes of the particle sensing surface.

3. A particle detector as claimed in claim 1, wherein the height of the projections varies.

4. A particle detector as claimed in claim 1, wherein the particle sensing surface is provided on the first substrate layer and wherein a second substrate layer is provided for detecting the presence of particles proximate to or in contact with the particle sensing surface.

5. A particle detector as claimed in claim 4, wherein the second substrate layer includes one of an array of exposed gate charge sensing field effect transistors with alternating voltage, an array of light emitting diodes (LEDs), or remote detection of spatial ionisation or luminescence of the particles proximate to or in contact with the particle sensing surface.

6. A particle detector as claimed in claim 5, wherein the projections are electrically isolated from the particle sensing surface.

7. A particle detector as claimed in claim 1, wherein means for applying a voltage potential across the particle sensing surface is provided.

8. A particle detector as claimed in claim 1, wherein the detector is adapted to discriminate between a range of particles having sizes ranging upwards from 10 nm.

\* \* \* \* \*